United States Patent [19]

Boullais et al.

[11] Patent Number: 5,344,767
[45] Date of Patent: Sep. 6, 1994

[54] PROCESS FOR PREPARING SULFIDES AND AMINO ACIDS LABELED WITH SULFUR-35

[75] Inventors: Claude Boullais, Gavdry; Jean-Pierre Noël, Clanche; Michel Riva, La Fontaine, all of France

[73] Assignee: Commissariat a l'Energie Atomique, Paris, France

[21] Appl. No.: 905,561

[22] Filed: Jun. 29, 1992

[30] Foreign Application Priority Data

Jul. 1, 1991 [FR] France .................. 91 08174

[51] Int. Cl.$^5$ .................. C12P 13/04; C12P 13/12
[52] U.S. Cl. .................. 435/106; 435/113; 424/9; 562/557; 562/559
[58] Field of Search .................. 424/1.1, 9; 435/106, 435/113

[56] References Cited

U.S. PATENT DOCUMENTS 2,970,893  2/1961  Viles .
4,649,039  3/1987  Garlick et al. .................. 424/1.1

FOREIGN PATENT DOCUMENTS 0181061  8/1985  European Pat. Off. .

OTHER PUBLICATIONS

Suarez, C. et al., "Preparation of carrier-free 35SH2 through direct reduction of the 35SO4-contained in neutron irradiated KCl" Radiochimica Acta, v6n3113-114 (1966).

Von Erichsen, L. C., et al. "Preparation and analytical control of H2S(35) of high specific activity" Radioisotopy 12:1019-1027 (1971).

Novopashin, V. M., "Reducing of sulphuric acid to hydrogen sulphide-by hydrogen at raised temp. using aluminium-cobalt-molybdenum, catalyst" Soviet Patents Abstracts, Section Ch, Week 8806 (1987).

Primary Examiner—Herbert J. Lilling
Attorney, Agent, or Firm—Viviana Amzel

[57] ABSTRACT

A method of preparing a high specificity $^{35}$S-sulfide comprises preparing a reducing mixture comprising hydrochloric acid, hydriodic acid and hypophosphorus acid, substantially removing any sulfate present in the mixture, admixing the reducing mixture with a composition comprising an $^{35}$S-sulfate corresponding to a desired $^{35}$S-sulfide to obtain the $^{35}$S-sulfide, and recovering the $^{35}$S-sulfide from the admixture. The thus prepared $^{35}$S-sulfides are applicable to the synthesis of high specificity $^{35}$S amino acids and derivatives thereof by sulfhydrylation, e.g., in the presence of an enzyme and a $^{35}$S-sulfide or sulfhydric acid and the O-acetylated amino acid. The labeled amino acid may be separated from the reaction mixture by reverse phase chromatography.

17 Claims, No Drawings

PROCESS FOR PREPARING SULFIDES AND AMINO ACIDS LABELED WITH SULFUR-35

BACKGROUND OF THE INVENTION

1. Field of the Invention

The invention relates to a new process for preparing sulfides labeled with sulfur-35, and for preparing amino acids and their derivatives labeled with sulfur-35, with high specific activity.

2. Description of the Background

The sulfur-containing amino acids L-cysteine and L-methionine play an important role in many biological processes, and in particular are incorporated in very varied proteins. The initiation of the biosynthesis of a polypeptide chain requires the presence of L-methionine; L-cysteine is necessary in the formation of disulfide bridges which stabilize the tertiary structure of proteins and also intervene at the active sites of many enzymes.

Sulfur-containing amino acids labeled with sulfur-35, and in particular methionine, are therefore very frequently used for the study of biological processes. In order to be used, it is necessary to have available products with a high specific activity, greater than 29.6 TBq to 37 TBq/mmole (800 to 1000 Ci/mmole)o Two types of processes are known which make it possible to obtain L-cysteine and L-methionine labeled with sulfur-35: the chemical route and the microbiological route.

Methods of synthesis by the chemical route are currently little used, for their yield is low; they require a lot of equipment, many stages of handling, and are not suited to the handling of very small quantities of reagents which are employed for the manufacture of a final product of very high specific activity.

For example, the method described in the publication Heise and Mittag [Kernenergie, 8, 181–184 (1965)] produces ($^{35}$S) L-methionine with a specific activity of 2775 MBq/mmole (75 mCi/mmole).

L-Cysteine and L-methionine labeled with sulfur 35 which is currently commercially available are prepared by the microbiological route.

Several publications describe this preparation method; the works of Albahari and Skakun-Todorovic [Journal of labelled compounds and Radiopharmaceuticals, XIV, 5, 727–733 (1978)], of Graham and Stanley [Analytical Biochemistry 47, 505–513, (1972)], of Bretscher and Smith [Analytical Biochemistry, 47, 310–312, (1972)] may be mentioned as examples.

Microorganisms (yeasts or bacteria) are cultured in minimum medium, the only source of sulfur being supplied by sodium or ammonium sulfate, labeled with sulfur-35, with a high specific activity.

The sulfur-35 is incorporated in the proteins, which are then hydrolyzed and the sulfur-containing amino acids are purified, from the hydrolysate by chromatography. This chromatography stage does not, however, manage to totally remove the contamination by other, unlabeled amino acids, (for example L-valine or L-leucine), as well as by ($^{35}$S)-D-methionine Each of these contaminants represents 2 to 3% of the ($^{35}$S)-L-methionine preparation obtained.

On the other hand, this method of preparation is relatively lengthy; it takes at least 24 hours for the sulfur to be incorporated in the proteins; another delay of 24 hours is necessary for the hydrolysis of the proteins to be complete.

The preparations of amino acids labeled with sulfur-35 must be frequently replaced, for the half-life of sulfur-35 is relatively short, and ($^{35}$S)-L-methionine has little chemical stability and is very rapidly oxidized to L-methionine sulfoxide.

It is thus particularly desirable to have available a simple and easy method of use which makes it possible to prepare these compounds as and when required.

The Inventors, in seeking to solve this problem, have directed their work towards the development of a method of enzymatic synthesis.

Various metabolical routes which lead to the synthesis of sulfur-containing amino acids are known, as well as the enzymes which intervene in each of the stages of this synthesis: for a general review, see, for example, Methods in Enzymology, volume 143, (1987), Editors W. B. Jakoby and Griffith.

The organic sulfur of cysteine and methionine arises from inorganic sulfur which can be taken up by certain microorganisms and reduced, in fine to the sulfide form. The sulfides react with serine or homoserine (or their O-acyl derivatives) to give cysteine and homocysteine.

Various enzymes can catalyze this reaction: [for a detailed review, cf. Soda, Methods in Enzymology 143 453–457 (1987)].

For example, O-acetylserine sulfhydrylase (EC.4.2.99.8), cystathionine β-synthase (EC.4.2.1.22), O-acetylhomoserine (thiol)-lyase (EC.4.2.99.10), and so on, may be mentioned.

Although these enzymes are known and have been purified, their employment in the preparation of amino acids labeled with sulfur-35, and with a high specific activity, has never been proposed.

Indeed, although the reactions catalyzed by these enzymes can be easily carried out in vitro in the presence of substrates which are not radio-labeled, and when there are no particular requirements regarding reaction yield or the quality of the final product, the same does not apply, however, when these reactions must be carried out in the presence of radio-labeled substrates and while ensuring a high specific activity in the final product as well as a high chemical and radiochemical purity.

The problems to be solved in order to achieve this aim are many because it is necessary to limit as much as possible the number of necessary stages, each stage having, in addition, to be compatible with the preceding and following stages.

The principal problem which has to be solved in order to allow the use of the enzymatic reaction with the best results is that of the employment of a suitable labeled substrate with high specific activity.

The problem does not arise in the methods for preparing amino acids labeled by the bacteriological route, because the sulfur-35 used in these methods, obtained from the irradiation of potassium chloride according to the reaction $^{35}$Cl(n,p)$^{35}$S, is purified in the form of sulfate which can be taken up by bacteria.

However, the enzymes which synthesize the sulfur containing amino acids use sulfides as substrate and not sulfates. It is thus necessary to carry out, prior to the enzymatic reaction, the reduction of the sulfate to sulfide. However, this stage can lead to a significant reduction in the specific activity.

The inventors have now selected a reducing mixture and developed reaction conditions which allow the reduction of the sulfate to sulfide with a good yield, and without loss of specific activity.

SUMMARY OF THE INVENTION

The subject of the present invention is a method for preparing sulfides labeled with sulfur-35, with high specific activity, which method comprises:

preparing a reducing mixture comprising hydrochloric acid, hydriodic acid and hypophosphorous acid, said mixture removing from sulfate ions present in the latter; and admixing the reducing mixture with a composition comprising sulfate labeled with sulfur-35 to obtain sulfide labeled with sulfur-35; and recovering the sulfide labeled with sulfur-35.

Other objects, advantages and features of the present invention will become apparent to those skilled in the art from the following discussion.

DESCRIPTION OF THE PREFERRED EMBODIMENTS

Within the meaning of the present invention, sulfide is understood to mean hydrogen sulfide or one of its salts (for example metal sulfide) and sulfate is understood to mean sulfuric acid or one of its salts.

According to a preferred embodiment of the method in accordance with the invention, the reducing mixture pretreated by heating in a stream of an inert gas (nitrogen, helium, and the like). The sulfate ions present the reducing mixture are reduced and entrained, in the form of hydrogen sulfide, by the stream of inert gas.

According to a preferred arrangement of this embodiment, said reducing mixture is pretreated by heating for 30 minutes to 3 hours at a temperature of between 90° and 150° C.

According to another preferred embodiment of the process in accordance with the Invention, said mixture comprises between 40 and 60% by volume of pure hydriodic acid, between 20 and 30% by volume of pure hydrochloric acid, between 20 and 30% by volume of water and between 10 and 15% of hypophosphorous acid as a 50% (w/w) solution in water.

According to another preferred embodiment of the process in accordance with the invention, the sulfate labeled with sulfur-35 is reduced, by heating in a stream of inert gas, in the presence of the pretreated reducing mixture and the sulfide labeled with sulfur-35 which is evolved is recovered in the form of hydrogen sulfide.

According to a preferred embodiment, the sulfide labeled with sulfur-35 is collected by sparging the hydrogen sulfide into an aqueous solution of a strong base, the strong base/sulfur-35 molar ratio ranging between 5/1 and 80/1.

The sulfide labeled with sulfur-35 obtained as a result of the reduction has the same specific activity as the starting sulfate. It can be used as a substrate for an enzymatic reaction. To this end, it can be added to the reaction mixture either in the form of a salt, formed during the sparging, of the abovementioned strong base or directly, by releasing the hydrogen sulfide into the reaction mixture.

Another subject of the present invention is a process for preparing amino acids labeled with sulfur-35, which method comprises a stage in the course of which the sulfhydrylation of serine or of homoserine, or of one of their O-acyl derivatives, is carried out by a sulfide labeled with sulfur-35 obtained by the process in accordance with the invention, in the presence of an enzyme capable of catalyzing said sulfhydrylation reaction.

As was said above, different enzymes can use the sulfides as substrates for the synthesis of sulfur-containing amino acids.

According to a preferred embodiment of the present invention, the enzyme O-acetyl-L-homoserine sulfhydrylase is used in the presence of O-acetyl-L-serine or of O-acetyl-L-homoserine.

This enzyme can be purified from S. Cerevisiae according to the method described by Yamagata [Methods in Enzymology 143, 478–483, (1987)]. It can also be obtained from other microorganisms containing it [Paszewski and Grabski, Acta Biochimica Polonica, 23, 321–324 (1976)].

This enzyme, also called O-acetyl-L-serine-O-acetyl-L-homoserine sulfhydrylase, catalyzes the following reactions: O-acetyl-L-serine + $H_2S$ → L-cysteine + $CH_3$COOH   O-acetyl-L-homoserine + $H_2S$ → L-homocysteine + $CH_3$COOH.

According to another preferred embodiment of the present invention, the product of the enzymatic reaction, labeled with sulfur-35, is purified by reversed phase chromatography of the reaction mixture.

According to another preferred embodiment of the present Invention, in order to obtain methionine labeled with sulfur-35, the methylation of the homocysteine obtained as a result of the enzymatic reaction is carried out prior to the purification by chromatography.

This methylation can be carried out in a way known per se, by a chemical route, for example by methyl iodide, or by an enzymatic route, for example by using homocysteine S-methyltransferase described by Shapiro et al. [The Journal of Biological Chemistry, 239, 5, 1551–1556, (1964)].

If the preparation of ($^{35}S$)-L-cystein or ($^{35}S$)-L-homocystein is desired, the oxidation of the ($^{35}S$)-L-cysteine or of the ($^{35}S$)-L-homocysteine obtained as a result of the enzymatic reaction is carried out.

The present Invention will be better understood with the help of the additional description which will follow, which refers to an example of the use of the process in accordance with the Invention.

It is self-evident, however, that this example is given solely as an illustration of the subject of the Invention, of which it does not in any way constitute a limitation.

EXAMPLES

EXAMPLE 1

Reduction of ($^{35}S$)- Sulfuric Acid or of One of its Salts to Hydrogen ($^{35}S$)-Sulfide ($^{35}S$)-Sulfuric acid having a specific activity of 46.2 TBq/mmole (1250 Ci/mmole), or one of its salts, obtained in a fashion known per se, for example by irradiation of KCl according to the nuclear reaction $^{35}Cl(n,p)^{35}S$, is reduced quantitatively to hydrogen ($^{35}S$)-sulfide in the presence of a reducing mixture whose composition is as follows:

5.3 ml of distilled or deionized (18 megohms) water
4.7 ml of hydrochloric acid (d=1.19)
10 ml of hydriodic acid (d=1.7)
2.5 ml of hypophosphorous acid in 50% solution.

After preparing the reducing mixture, 5 ml of the latter are introduced into a reactor under an inert atmosphere of helium.

Under these conditions, the sulfate ions present in the reactants which constitute this mixture are reduced to sulfide ions and removed from the mixture, as they are formed, in the form of a gas, (H$_2$S), by heating to 110° C. for 45 min in a stream of helium at a flowrate of 0.9 l/h. The solution is then cooled to room temperature. More than 99% of the sulfate ions are thus removed.

After cooling, 200 μl (14.86 GBq=400 mCi) of the solution containing the ($^{35}$S)-sulfuric acid (2 Ci/ml) or one of its salts are introduced into the pretreated reducing mixture and are treated by heating in a stream of helium, as described above, at a helium flowrate of 0.4 l/h.

The hydrogen ($^{35}$S)-sulfide is obtained with a specific activity identical to that of the starting sulfuric acid and is collected in an aqueous solution, cooled in ice, containing sodium hydroxide (20 μmoles of sodium hydroxide for about 0.3 μmole of $^{35}$S). The yield of the reducing reaction is 99.8%; that is to say, that there is found in the reducing mixture, as a result of the reaction, only 0.2% of the activity introduced into the reaction mixture. On the other hand, 85% of the total activity of the ($^{35}$S)-sulfuric acid is present in the sodium hydroxide solution which has been used to trap the hydrogen sulfide.

EXAMPLE 2

Enzymatic Reaction

After addition of 5 μl of TRIS-HCl (1M) pH=7.8 to the solution containing the sodium ($^{35}$S)-sulfide, the latter is neutralized by a dilute (0.1N) hydrochloric acid solution, to pH=7.8.

The following products, which are necessary for the enzymatic reaction, are then introduced into the radioactive solution:

1 μl of pyridoxal phosphate (5.3 mg/ml)
100 μl of O-acetyl-L-homoserine (16.1 mg/ml)
2 μl of dithiothreitol (154 mg/ml)
5 μl of a preparation containing 2.4 mg of protein/ml, of O-acetyl-L-homoserine sulfhydrylase enzyme (specific activity: 0.135 μmol of homocysteine/min/mg of protein).

The total volume of the reaction mixture is approximately 1 ml.

The pH is checked and adjusted to 7.8 if necessary before introducing the enzyme.

The O-acetyl-L-homoserine sulfhydrylase was purified according to the method described by Yamagata (abovementioned publication) from a strain of *Saccharomyces cerevisial*, by fractional precipitation in a medium containing ammonium sulfate and then by passage through a DEAE-cellulose column. This enzyme is relatively stable and can be stored cooled to −80° C. for many months without significant loss of its activity.

After addition of the enzyme, the reaction mixture is left at room temperature for 1 hour.

EXAMPLE 3

Methylation Reaction

After the enzymatic reaction, 5 μl of pure methyl iodide, the methylating agent, and then 25 μl of 1N sodium hydroxide are added directly to the reaction mixture. The latter is left at room temperature for 30 minutes.

EXAMPLE 4

Purification of ($^{35}$S)-L-Methionine

After the methylation reaction, the reaction mixture is directly injected, without prior treatment onto a semi-preparative column 25 cm long (Zorbax C18) containing a reversed phase support, equipped with a precolumn 2 cm long containing the same support. The eluent used is distilled and deionized (18 megohms) water at a flowrate of 3 ml/min. The operation is carried out under a helium atmosphere. The radioactive fraction containing the ($^{35}$S)-L-methionine with high specific activity is collected while cooled under an argon atmosphere.

The ($^{35}$S)-methionine is eluted after 8 to 10 minutes, under the chromatography conditions indicated above.

Analysis of the fraction containing the ($^{35}$S)-L-methionine by various chromatographic techniques shows that it does not contain other, labeled or unlabeled, amino acids.

The yield of purified ($^{35}$S)-L-methionine from ($^{35}$S)-sulfuric acid is of the order of 10 to 15% of the total activity of the sulfuric acid i.e. 40 to 60 mCi. The specific activity of the purified L-methionine is identical to that of the starting sulfuric acid.

The invention now being fully described, it will be apparent to one of ordinary skill in the art that many changes and modifications can be made thereto without departing from the spirit or scope of the invention as set forth herein.

We claim:

1. A method of preparing a high specificity $^{35}$S amino acid or derivative thereof, comprising
    preparing a reducing mixture comprising hydrochloric acid, hydriodic acid and hypophosphorus acid;
    substantially removing any sulfate present in the mixture;
    admixing the reducing mixture with a composition comprising a $^{35}$S-sulfate to obtain a $^{35}$S-sulfide; and
    sulfhydrylating an amino acid or derivative thereof with the $^{35}$S-sulfide in the presence of a sulfhydrylating enzyme.

2. The method of claim 1, wherein the sulfate ions present in the reducing mixture are removed by
    heating in an inert atmosphere and reducing the sulfate to sulfide; and
    removing the sulfide from the reducing mixture by providing the inert gas as a stream.

3. The method of claim 2, wherein
    the reducing mixture is heated at a temperature of about 90° to 150° C.

4. The method of claim 3, wherein
    the reducing mixture is heated for a period of about 30 min to 3 hrs.

5. The method of claim 1, wherein the reducing mixture comprises about 20 to 30 v % pure hydrochloric acid;
    about 40 to 60 v % pure hydriodic acid;
    about 10 to 15 v % of a 50 wt. % aqueous solution of pure hydrophosphorus acid; and
    about 20 to 30 v % water.

6. The method of claim 1, wherein
    the admixing step is conducted under heat in a stream of inert gas; and
    the $^{35}$S-sulfide is recovered as $^{35}$S—SH$_2$.

7. The method of claim 1, wherein
    the $^{35}$S-sulfide comprises $^{35}$S—SH$_2$; and
    the $^{35}$S—SH$_2$ is recovered as a $^{35}$S salt by sparging into a strong alkaline solution, the proportion of the strong base to the $^{35}$S—SH$_2$ being about 5:1 to 80:1.

8. The method of claim 1, wherein the $^{35}$S-sulfide used to sulfhydrylate the amino acid or derivative thereof comprises a sulfide selected from the group consisting of SH$_2$ and sulfide salts.

9. The method of claim 1, wherein the enzyme comprises O-acetyl-L-homoserine sulfhydrylase; and the amino acid derivative comprises O-acetyl-L-serine or O-acetyl-L-homoserine.

10. The method of claim 1, further comprising recovering the $^{35}$S-amino acid from the reaction mixture.

11. The method of claim 10, wherein the $^{35}$S-sulfide is recovered by reverse phase chromatography.

12. A method of obtaining a high specificity $^{35}$S-homocysteine comprising the method of claim 9, wherein the amino acid derivative comprises O-acetyl-L-homoserine, and the enzyme comprises O-acetyl-L-homoserine sulfhydrylase to obtain $^{35}$S-homocysteine.

13. The method of claim 12, further comprising recovering the $^{35}$S-homocysteine from the reaction mixture by reverse phase chromatography.

14. A method of obtaining a high specificity $^{35}$S-methionine comprising the method of claim 12; and methylating the thus obtained $^{35}$S-homocysteine to obtain $^{35}$S-methionine.

15. The method of claim 14, further comprising recovering the $^{35}$S-methionine from the reaction mixture by reverse phase chromatography.

16. A method of obtaining a high specificity $^{35}$S-cysteine, comprising the method of claim 9, wherein the amino acid derivative comprises O-acetyl-L-serine to obtain $^{35}$S-cysteine.

17. The method of claim 16, further comprising recovering the $^{35}$S-cystein from the reaction mixture by reverse phase chromatography.

* * * * *